(12) United States Patent
Martin

(10) Patent No.: US 7,972,371 B2
(45) Date of Patent: Jul. 5, 2011

(54) MAGNETIC RESONANCE COMPATIBLE STENT

(75) Inventor: Alastair J. Martin, Novato, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1398 days.

(21) Appl. No.: 10/542,975

(22) PCT Filed: Dec. 19, 2003

(86) PCT No.: PCT/IB03/06365
§ 371 (c)(1),
(2), (4) Date: Jul. 21, 2005

(87) PCT Pub. No.: WO2004/066803
PCT Pub. Date: Aug. 12, 2004

(65) Prior Publication Data
US 2006/0136039 A1  Jun. 22, 2006

Related U.S. Application Data

(60) Provisional application No. 60/444,302, filed on Jan. 31, 2003.

(51) Int. Cl.
*A61F 2/06* (2006.01)

(52) U.S. Cl. .................................... 623/1.15

(58) Field of Classification Search .............. 623/1.15, 623/1.17, 1.11, 1.34; 606/195, 198
See application file for complete search history.

(56) References Cited

U.S. PATENT DOCUMENTS

| | | | |
|---|---|---|---|
| 4,856,516 A * | 8/1989 | Hillstead | 606/194 |
| 5,964,705 A | 10/1999 | Truwit et al. | |
| 6,066,168 A * | 5/2000 | Lau et al. | 623/1.16 |
| 6,119,032 A | 9/2000 | Martin et al. | |
| 6,171,240 B1 | 1/2001 | Young et al. | |
| 6,231,516 B1 * | 5/2001 | Keilman et al. | 600/485 |
| 6,275,722 B1 | 8/2001 | Martin et al. | |
| 6,280,385 B1 | 8/2001 | Melzer et al. | |
| 6,397,094 B1 | 5/2002 | Ludeke et al. | |
| 6,514,285 B1 * | 2/2003 | Pinchasik | 623/1.22 |
| 6,626,933 B1 * | 9/2003 | Lau et al. | 623/1.11 |
| 2002/0171424 A1 * | 11/2002 | Morich et al. | 324/318 |
| 2002/0188345 A1 | 12/2002 | Pacetti | |
| 2003/0001575 A1 * | 1/2003 | Cheng et al. | 324/318 |
| 2003/0088178 A1 * | 5/2003 | Owens et al. | 600/420 |
| 2003/0181972 A1 * | 9/2003 | Jansen et al. | 623/1.15 |
| 2005/0049683 A1 * | 3/2005 | Gray et al. | 623/1.15 |

FOREIGN PATENT DOCUMENTS

| | | |
|---|---|---|
| WO | WO 02/30331 A1 | 4/2002 |
| WO | WO 02/47575 A2 | 6/2002 |

\* cited by examiner

*Primary Examiner* — Anhtuan T Nguyen
*Assistant Examiner* — Thomas McEvoy

(57) ABSTRACT

An intravascular stent (50) is provided for use in conjunction with a magnetic resonance imaging system. The stent is constructed to minimize the radio-frequency cage effect which results from currents being induced in stents when subjected to magnetic resonance related radio frequency signals. The stent includes a mesh of electrically conductive material and a non-conductive material disposed within the mesh for connecting the mesh in a generally tubular arrangement such that a net current flowing through the mesh is approximately zero and the RF cage effect is minimized.

9 Claims, 3 Drawing Sheets

MAGNETIC RESONANCE COMPATIBLE STENT

CROSS REFERENCE TO RELATED APPLICATIONS

This application claims the benefit of U.S. provisional application Ser. No. 60/444,302 filed Jan. 31, 2003, which is incorporated herein by reference.

The present invention relates to the field of magnetic resonance imaging (MRI). It finds further application in conjunction with magnetic resonance arteriography in which arteries and surrounding tissues are assessed for coronary and vascular diseases such as atherosclerosis. More specifically, the invention relates to the use of stents for use in treating such diseases and for minimizing image artifacts which can be caused by stents during magnetic resonance procedures.

Magnetic resonance imaging (MRI) is increasingly used to assess vascular disease due to its non-invasive nature. In magnetic resonance imaging, a substantially uniform main magnetic field is generated within an examination region. The main magnetic field polarizes the nuclear spin system of a patient being imaged within the examination region. Magnetic resonance is excited in dipoles which align with the main magnetic field by transmitting radio frequency excitation signals into the examination region. Specifically, radio frequency pulses transmitted via a radio frequency coil assembly tip the dipoles out of alignment with the main magnetic field and cause a macroscopic magnetic moment vector to precess around an axis parallel to the main magnetic field. The radio frequency coil assembly is tuned to the resonance frequency of the dipoles to be imaged in the main magnetic field. The precessing magnetic moment, in turn, generates a corresponding radio frequency magnetic signal as it relaxes and returns to its former state of alignment with the main magnetic field. The radio frequency magnetic resonance signal is received by the radio frequency coil assembly which is again tuned to the resonance signal. From the received signals, an image representation is reconstructed for display on a human viewable display. Spatial position is encoded with magnetic field pulses that alter resonance frequency in accordance with spatial position.

With respect to the treatment of coronary and vascular diseases the implantation of stents has become a common procedure. A typical stent is a small, self or balloon expanding, metallic mesh tube that is placed within an artery to keep the vessel open. Such stents are often used to support tissues while healing takes place. They may also be used during coronary artery bypass graft surgery to keep the grafted vessel open, after balloon angioplasty to prevent re-closure of the blood vessel, or during/after other surgeries. Accordingly, stenting of atherosclerotic lesions has become an extremely popular therapy and is utilized in a wide assortment of anatomic locations.

While stents offer the advantages of being an effective minimally invasive therapy, they do suffer from significant restenosis rates. Therefore, routine diagnostic examinations must be performed following placement of a stent.

The concurrent increases in the use of MR for evaluating vascular disease and the use of stents in associated treatment have produced an unfortunate schism. Depending on the specific style of stent employed, MR visualization of tissue near or within a stent is either impossible or seriously impaired. Intravascular stents are based on cylindrical geometries due to the inherent morphology of the vessels in which they are placed. Due to the stringent mechanical requirements of stents, metallic materials are necessary. Since these devices are typically manufactured by etching a solid cylindrical former, electrical conductivity is unhindered in all directions within the stent. Accordingly, when exposed to radio-frequency (RF) electromagnetic energy as produced by an MR imager, currents will be induced in the stent. These induced currents locally distort the applied RF field and attenuate its amplitude within the stent (RF shielding effect). Therefore, a major limiting factor of these conductive substances, in addition to their magnetic susceptibility, is their interaction with the applied radio-frequency (RF) pulses used in MR to excite tissue. In general terms, the external RF field produces currents within the stent that tend to oppose the external field. This interaction distorts the RF field near the stent, and commonly results in a marked reduction in signal intensity from within its linnen. This effect is also commonly referred to as the "RF cage effect" and limits the utility of non-invasive follow-up of stent patency and artery assessment by MRI.

It is therefore desirable to have a stent design that can overcome interference problems with the transmitted radio-frequency field of MR imagers, making it possible to evaluate patients with MR after stent therapy.

Those skilled in the art will, upon reading and understanding the appended description, appreciate that aspects of the present invention address the above and other matters.

In accordance with one aspect of the invention, an intravascular stent is provided. The stent includes a mesh of electrically conductive material. The stent also includes non-conductive material disposed within the mesh for connecting the mesh in a generally tubular arrangement such that a net current flowing through the mesh is approximately zero.

In accordance with a more limited aspect of the invention, wherein the mesh of electrically conductive material includes a number of struts disposed in generally diagonal directions with respect to a central axis of the stent.

In accordance with a more limited aspect of the invention, the non-conductive material comprises a plurality of connector elements for channeling a current through the plurality of struts.

In accordance with a more limited aspect of the invention, the current flowing through the struts is induced by RF signals within an examination region of a magnetic resonance apparatus.

In accordance with a more limited aspect of the invention, the struts and connector elements define a plurality of strut segments, each strut segment having a segment current associated therewith and the segment currents in adjacent strut segments are equal in magnitude and opposite in polarity.

In accordance with a more limited aspect of the invention, the conductive mesh comprises a plurality of co-axial loops and a plurality of linking members for connecting the co-axial loops.

In accordance with a more limited aspect of the invention, the non-conductive material comprises a plurality of insulating nodes. The insulating nodes are disposed within the conductive mesh such that a plurality of open circuits are formed in the mesh.

In accordance with a more limited aspect of the invention, the non-conductive material includes a plurality of insulating nodes, the insulating nodes disposed within the conductive mesh. The stent further includes a plurality of channeling elements disposed within the insulating nodes, the channeling elements for directing an induced current through the conductive mesh.

In accordance with another aspect of the invention, a magnetic resonance compatible stent is provided for use in intravascular therapy. The stent includes a plurality of electrically conductive elements arranged in a generally tubular structure and at least one non-conductive insulator disposed among the conductive elements for directing a current flowing in the conductive elements such that a net current flowing in the stent is approximately zero.

In accordance with a more limited aspect of the invention, the current is induced by RF signals in an examination region of a magnetic resonance apparatus.

In accordance with a more limited aspect of the invention, the conductive elements includes generally diagonally arranged struts with respect to a central axis of the stent and the at least one non-conductive insulator includes a plurality of connector elements for directing the current through the struts whereby adjacent segment currents cancel each other.

In accordance with a more limited aspect of the invention, the conductive elements include a plurality of loops disposed about a central axis of the stent; and a plurality of linking members for joining the loops such that the loops and linking members form a generally tubular structure around the central axis of the stent, and at least one non-conductive insulator includes a plurality of insulating nodes disposed within the conductive elements to control the current induced in the conductive elements.

In accordance with a more limited aspect of the invention, the stent further includes a plurality of channeling elements disposed within the insulator nodes. The channeling elements direct the current through the loops and linking members so that currents flowing in adjacent loops cancel each other.

In accordance with another aspect of the invention, a magnetic resonance compatible stent is provided. The stent includes conducting means for conducting a current in the stent, the current being induced by RF signals from within an examination region of a magnetic resonance apparatus and non-conducting means for directing the current flowing in the stent such that a net current flowing in the stent is approximately zero.

In accordance with another aspect of the invention, a method of magnetic resonance imaging is provided. The method includes the steps of generating a main magnetic field within an examination region using a main magnet, exciting magnetic resonance in a subject disposed in the examination region by transmitting RF signals into the examination region, the subject having an intravascular stent disposed therein, spatially encoding the magnetic resonance in the subject via magnetic field gradients, and receiving magnetic resonance signals from the subject. The method also includes inducing a current in the intravascular stent from at least one of the transmitted RF signals and the magnetic resonance signals from the subject and directing the induced current through the stent whereby a net current flowing through the stent in approximately zero. The method also includes reconstructing the received signals into a magnetic resonance image.

One advantage of an embodiment of the invention is that it makes it possible to minimize or possibly even block entirely RF interactions in stents when the stents are subject to magnetic resonance imaging techniques.

Another advantage of an embodiment of the invention is that stent-related artifacts in magnetic resonance imaging may be reduced.

Another advantage of an embodiment of the invention is that it makes it more practical to follow patients with non-invasive MR imaging following stent therapy.

Another advantage of an embodiment of the invention is that construction of the stent is facilitated.

Still further advantages of the present invention will become apparent to those of ordinary skill in the art upon a reading and understanding of the following description of the preferred embodiments.

The invention may take form in various components and arrangements of components, and in various steps and arrangements of steps. The drawings are only for purposes of illustrating a preferred embodiment and are not to be construed as limiting the invention.

Figure 1:
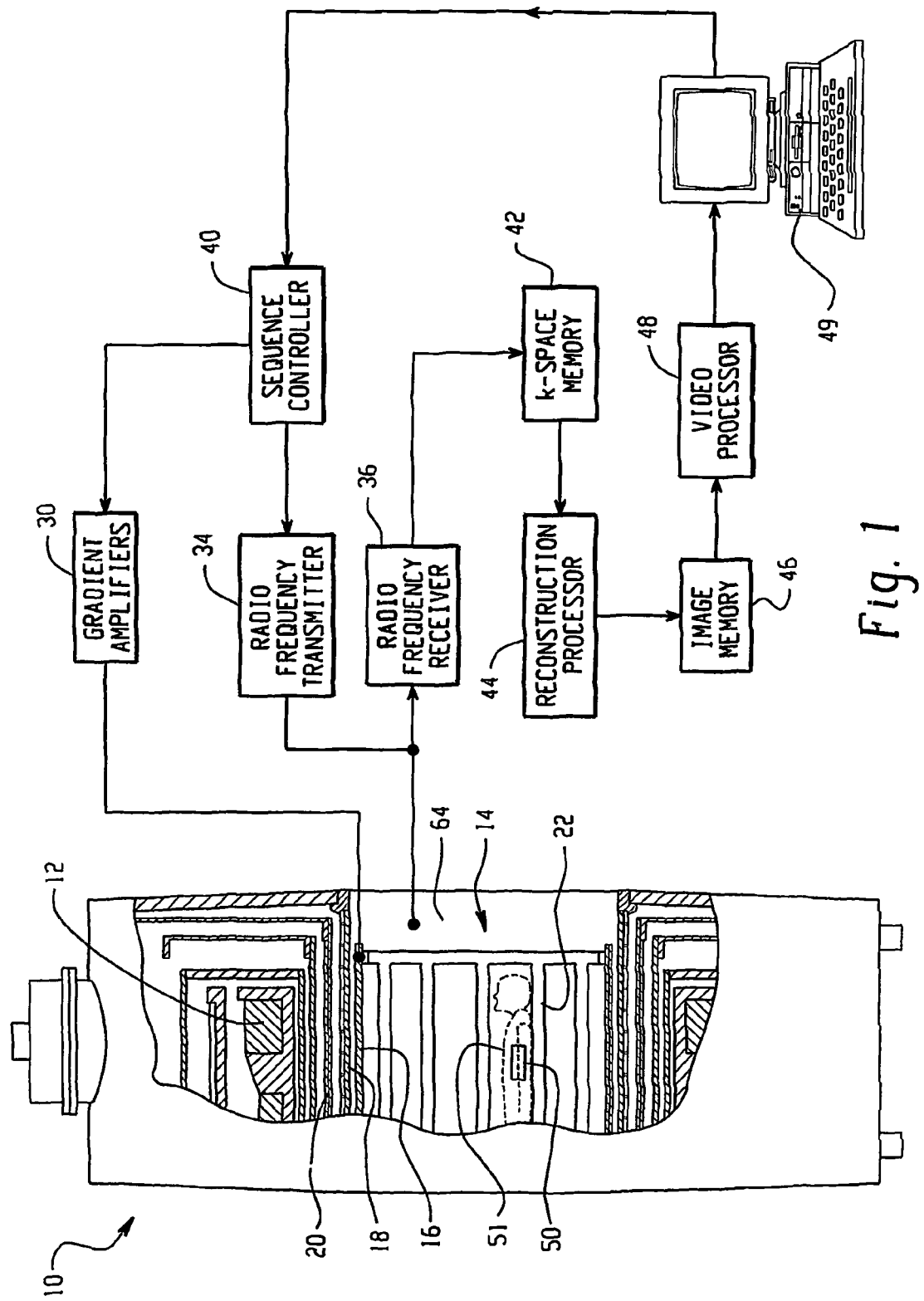
FIG. 1 is a diagrammatic illustration of an MRI scanner having a stent in the imaging region.

With reference to FIG. 1, a magnetic resonance imaging scanner 10 includes a cylindrical main magnet 12, which is preferably superconducting and cryoshielded. The main magnet 12 defines a magnet bore 14, or examination region, inside of which a patient 51 or other imaging subject is placed for imaging. The main magnet 12 produces a spatially and temporally constant and uniform main magnetic field oriented along a longitudinal axis of the bore 14. Instead of a superconducting magnet, a non-superconducting magnet can be used. Moreover, a vertical magnet, an open magnet, or other type of main magnet can be employed instead of the illustrated horizontal cylindrical main magnet 12.

Magnetic field gradient coils include a primary gradient coil 16 and optionally a shield gradient coil 18 that cooperatively produce magnetic field gradients in the bore 14 for spatially encoding magnetic resonance signals, for producing magnetization-spoiling field gradients, or the like. Preferably, the magnetic field gradient coils 16, 18 include coils configured to produce magnetic field gradients in three orthogonal directions including transverse x- and y-directions. In addition to the shield coil 18, an optional cold shield 20 provides a high conductivity eddy current surface for residual gradient fields thus protecting the magnet coils still further away. In a suitable embodiment, the cold shield 20 is integrated into a housing of the main magnet 12.

A radio frequency coil assembly 22, for example a whole body coil, generates radio frequency pulses for exciting magnetic resonances. The radio frequency coil assembly 22 can also serve to detect magnetic resonance signals. Optionally, additional local radio frequency coils or phased radio frequency coil arrays (not shown) are included for exciting and/or detecting magnetic resonances at localized areas in the bore 14.

Gradient pulse amplifiers 30 deliver controlled electrical currents to the magnetic field gradient coils 16, 18 to produce selected magnetic field gradients. A radio frequency transmitter 34, preferably digital, applies radio frequency pulses or pulse packets to the radio frequency coil assembly 22 to generate selected magnetic resonance excitations. A radio frequency receiver 36 also coupled to the radio frequency coil assembly 22 receives magnetic resonance signals. If more than one radio frequency coil is provided (such as a local coil or phased coil array), then different coils are optionally used for the magnetic resonance excitation and detection operations.

To acquire magnetic resonance imaging data of a subject, the subject is placed inside the magnet bore 14, preferably at or near an isocenter of the main magnetic field. A sequence controller 40 communicates with the gradient amplifiers 30 and the radio frequency transmitter 34 to produce selected transient or steady state magnetic resonance configurations in the subject, to spatially encode such magnetic resonances, to selectively spoil magnetic resonances, or otherwise generate selected magnetic resonance signals characteristic of the subject. The generated magnetic resonance signals are detected by the radio frequency receiver 36, and stored in a k-space memory 42. The imaging data is reconstructed by a reconstruction processor 44 to produce an image representation that is stored in an image memory 46. In one suitable embodiment the reconstruction processor 44 performs an inverse Fourier transform reconstruction.

The resultant image representation is processed by a video processor 48 and displayed on a user interface 49, which is preferably a personal computer, workstation, or other type of computer. Rather than producing a video image, the image representation can be processed by a printer driver and printed, transmitted over a computer network or the Internet, or the like. Preferably, the user interface 49 also allows a radiologist or other operator to communicate with the magnetic resonance sequence controller 40 to select magnetic resonance imaging sequences, modify imaging sequences, execute imaging sequences, and so forth.

Figure 2:
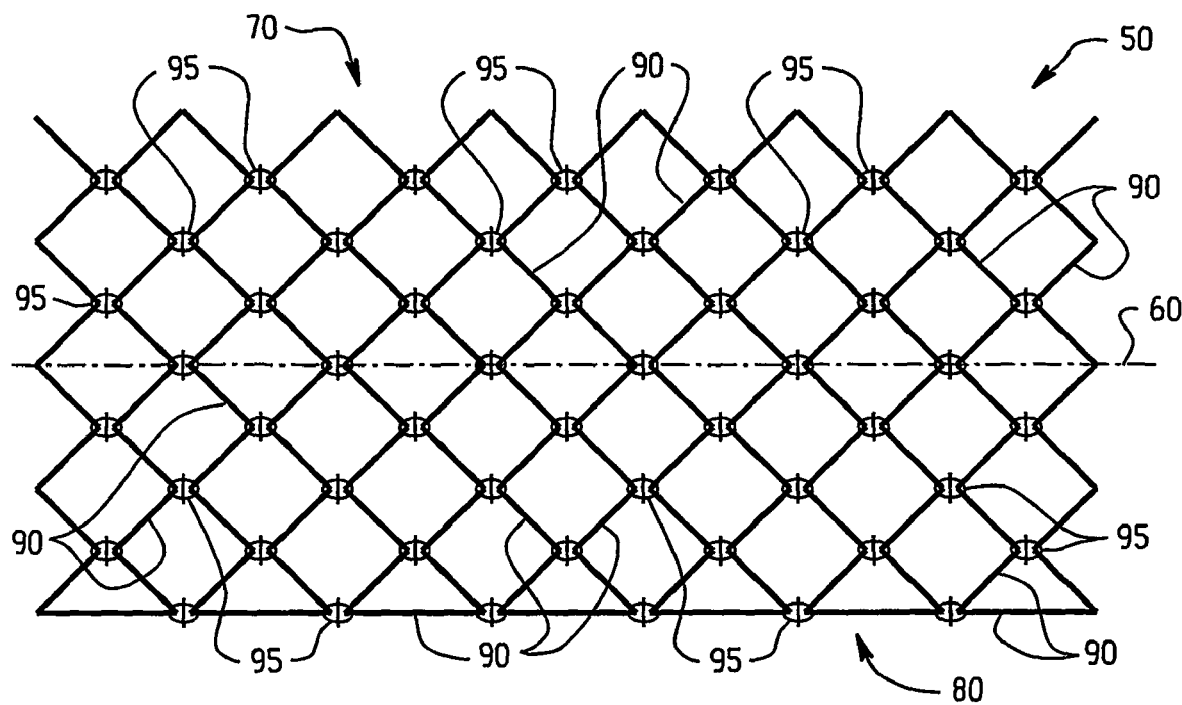
FIG. 2 is an illustration of an embodiment of a stent, in accordance with the invention.

Continuing with FIG. 1 and with more particular regard to FIG. 2, a stent 50 is shown. In general, stents may be considered as cylindrical metallic cages oriented in a random orientation within the human body. Since the dimensional scale of stents is very small in comparison to the RF wavelengths associated with typical MR scanners, a DC approximation can be employed. Accordingly, if a conductor pattern is created such that RF pickup of one part of the stent is exactly cancelled by another part of the stent, then external RE fields (e.g.—RF coil transmissions) will induce no net current in the stent 50. The effect of such a design is that the RF cage effect is effectively blocked.

FIG. 2 shows one such embodiment of a stent 50 in which net current flow due to an induced current is substantially cancelled. For the purpose of describing the structure of the stent 50, FIG. 2 shows the stent 50 in a laid open, planar view. One skilled in the art will appreciate that in use, the stent is wrapped around its central axis 60 to form a generally cylindrical, or tubular, structure where the top portion 70 of the stent is connected to the bottom portion 80 of the stent such that the stent 50 forms such a cylinder.

Continuing with FIG. 2, the stent 50 is made up of an electrically conductive mesh which is connected by non-conductive material. Materials which can be used for constructing the conductive mesh include stainless steel, platinum and nickel titanium alloys. Materials which can be used for the non-conductive material include, for example, non-conductive polymer epoxies.

In the embodiment shown, the conductive mesh includes struts 90, arranged in diagonal directions, as shown, and the non-conductive material includes connector elements, or insulator nodes, 95, for connecting the struts. By arranging the struts and connector elements appropriately, a net current which may flow through the stent 50 is minimized. The vertical lines drawn through the connector elements in FIG. 2 are for the purpose of illustration only and indicate that current through the connector elements can flow generally vertically and cannot flow generally horizontally. Such an arrangement is shown in more detail in FIGS. 3A and 3B.

Figure 3A:
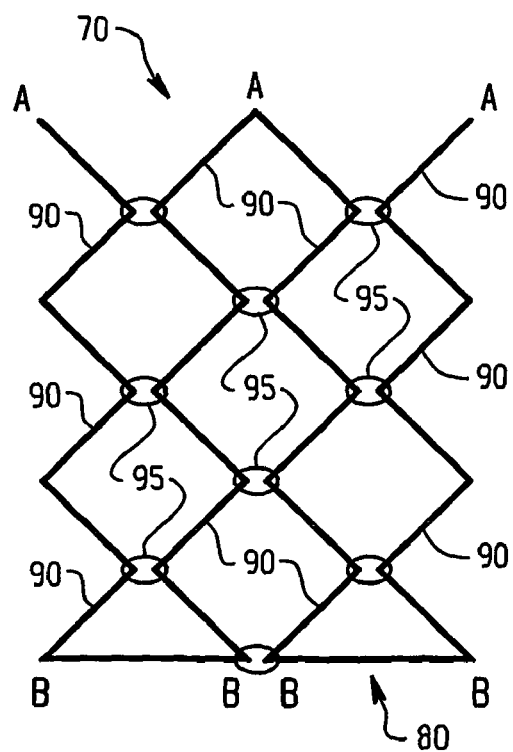
FIG. 3A is an illustration of a section of a stent, in a more detailed view.

With respect to FIG. 3A, the arrangement of a portion of the stent can be seen in detail. As can be seen, the struts 90 are interconnected by connectors 95 such that there is a continuity between strut portions in a generally vertical direction with respect to the page of FIG. 3A and there is a discontinuity along the struts 90 in the diagonal direction. The gaps between the struts are exaggerated for illustrative purposes. One skilled in the art will appreciate that, when wrapped into its generally cylindrical form, there is no direct continuity between points A on the top portion 70 of the strut 50 and points B on the bottom portion 80 of the strut.

Figure 3B:
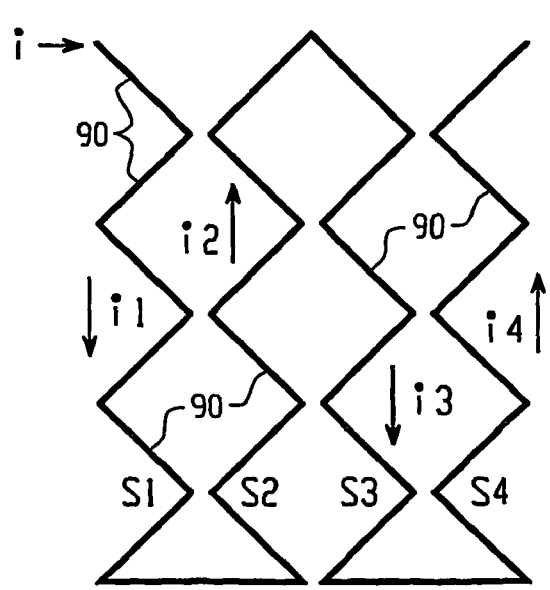
FIG. 3B is an illustration of a section of a stent, in a more detailed view, showing a current path through the stent.

The effect of such an arrangement can be seen in FIG. 3B. For conductive struts 90 and non-conductive connectors 95 (not shown for the purpose of this figure), a given current i passing though stent segments s1, s2, s3, and s4 can be represented by current segments i1, i2, i3, and i4. As can be seen, the individual adjacent currents flow with opposite polarity and cancel each other, thereby substantially canceling a net current in the stent 50. Accordingly, in the presence of a largely homogeneous RF field (as produced by an MR imager) the induced currents in adjacent segments will oppose one another, minimizing any net current flow. Otherwise the stent would be electrically conductive in multiple directions and the currents running through it would not necessarily cancel.

In general terms, the stent 50 is constructed to minimize the RF cage effect when used in conjunction with an MR system. In operation, the main magnetic field is generated in the examination region via control of the main magnet. Magnetic field gradients are established in the examination region in, for example, slice, phase, and read encode directions using the gradient magnet system. Radio frequency pulses are transmitted into the examination region to excite resonance in the subject disposed in the examination region. A sequence controller is used to control the gradients and RF transmissions in accordance with desired MR imaging sequences.

With regard to the present invention, a patient is located within the examination region. The stent 50 is also located within the examination region. This can be during an implantation process, where the stent 50 is typically compressed, inserted into a region of interest of the subject, and thereafter allowed to expand. Alternately, the stent 50 may already be implanted in the subject and the subject is being examined for the purpose of a follow-up evaluation at or near the site of a stent implantation.

Due to the RF signal transmission by the MR system and even to the RF signals from the subject, currents are induced in the stent 50. Because the induced currents travel through current patterns in accordance with the present invention, the net current in the stent 50 is effectively minimized. Therefore, subsequent resonance signals, and associated images, that are received from the area surrounding and from within the stent 50 are not negatively affected by the stent.

Figure 4A:
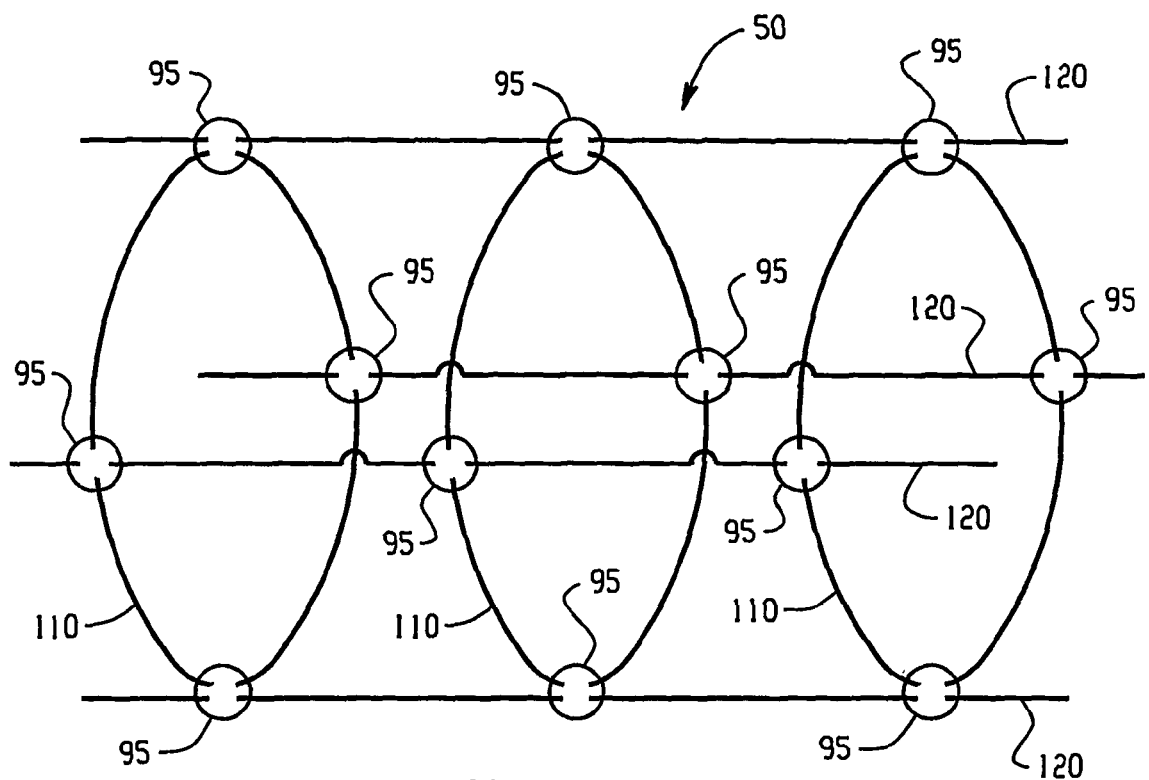
FIG. 4A is an illustration of another embodiment of a stent.
Figure 4B:
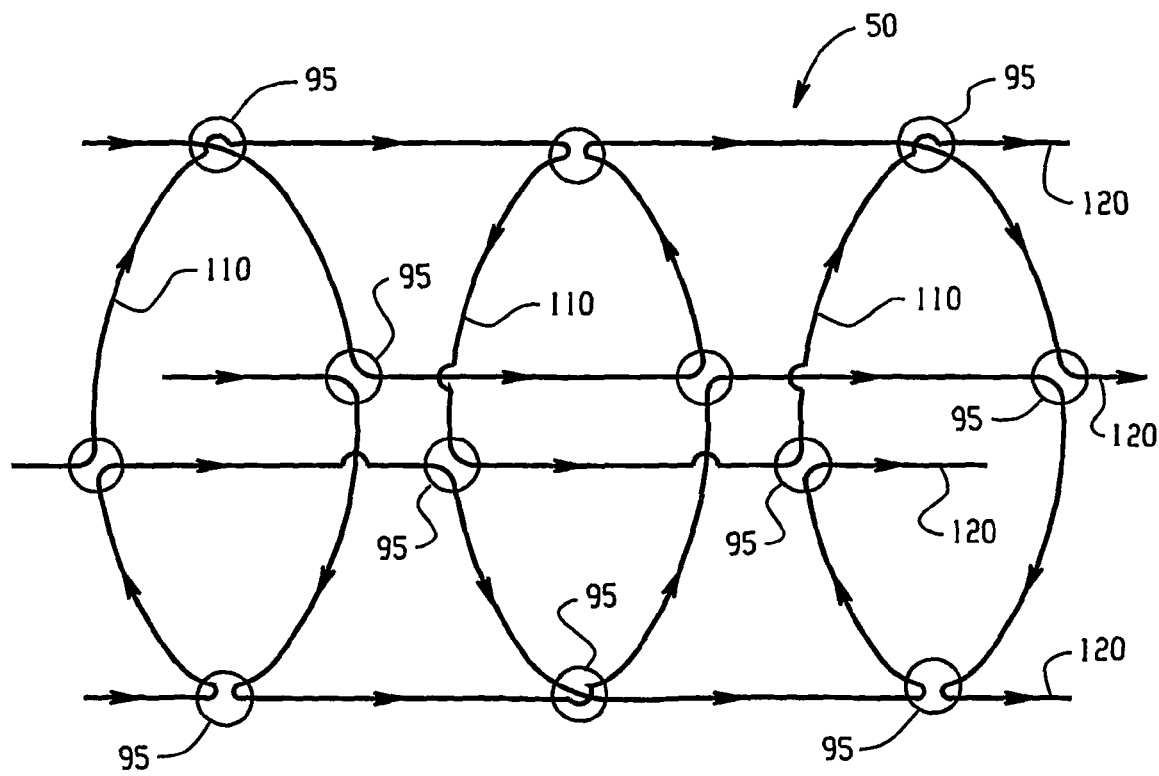
FIG. 4B is an illustration of another embodiment of a stent.

As one skilled in the art will appreciate, many different permutations of the control of current patterns described herein are envisioned. For example, other embodiments of the invention are shown in FIGS. 4A and 4B. In FIG. 4A a stent 50 is shown in which the conductive mesh is made up of a series of co-axial loops 110 connected by a number of linking members 120 to create a generally cylindrical, or tubular, former. The loop elements 110 are corrugated to allow for compression of the stent 50, but their overall shape remains annular. In order to control the current pathways within the stent 50, non-conductive material is provided in the form of insulating nodes 95 at the connection points, as shown. As can be seen the loop elements and the linking members are not connected. Therefore, the nodes 95 prevent current flow between different elements of the stent 50, thereby creating a mesh of open circuits and greatly reducing the RF cage effect associated with local shielding/distortion of external RF fields.

With respect to FIG. 4B, the current flow within the stent 50 can be channeled through the insulating nodes 95 by connecting the co-axial loops 110 and linking members 120 as shown. Here, the current, as indicated by the arrows in FIG. 4B, passing through individual loops 110 is opposed by the current passing through adjacent loops. This is accomplished by controlling the connectivity through the nodes 95 such that current pick-up on one loop element results in current flow of the opposite polarity in its nearest neighbor.

Regardless of the structure of the stent, a key to preventing the RF interaction with an MR system is to control the current pathways within the stent structure. Accordingly, another embodiment of the invention is to construct the stent in layers wherein the current passing through the first, or inner layer, cancels the current passing through the second, or outer layer. Accordingly, and in order to maintain the structural properties of the stent, it may be desirable to construct the conductive mesh in two layers, with a thin elastic layer of non-conductive material in between. This allows overlapping of stent conduction patterns that are diametrically opposed and therefore result in a substantially reduced net pick-up of external RF fields in comparison to typical stents.

Another embodiment of the invention involves a design wherein, generally speaking, the left half of the stent could be forced to conduct with the opposite polarity of the right half of the stent. Accordingly, the currents in the left half and the right half cancel each other, resulting in a substantially reduced net current.

The invention has been described with reference to the preferred embodiment. Obviously, modifications and alterations will occur to others upon reading and understanding the preceding description. It is intended that the invention be construed as including all such modifications and alterations insofar as they come within the scope of the appended claims or the equivalents thereof.

Having thus described the preferred embodiments, the invention is now claimed to be:

1. A magnetic resonance compatible stent for use in intravascular therapy, the stent comprising:
   a plurality of electrically conductive elements arranged in a generally tubular structure, the conductive elements comprising generally diagonally arranged struts with respect to a central axis of the stent to define a diamond-shaped mesh of the conductive elements, the conductive elements comprising:
   a plurality of zig-zag loops disposed about a central axis of the stent; and
   a plurality of linking members for joining the loops such that the loops and linking members form a generally tubular diamond-shaped conductive mesh cylinder around the central axis of the stent; and
   a plurality of non-conductive connector nodes disposed among the conductive elements for directing currents induced by RF signals in an examination region of a magnetic resonance apparatus to flow in the conductive elements such that the currents flowing in adjacent conductive elements cancel each other and a net current flowing in the stent is substantially minimized; wherein the loops and linking members are connected within the non-conductive connector nodes such that the current flowing through adjacent loops substantially cancel each other.

2. The stent according to claim 1, wherein each zig-zag loop is electrically connected to each neighboring zig-zag loop only once and mechanically connected at a plurality of locations by a plurality of the non-conductive connector nodes.

3. The stent according to claim 1, wherein each zig-zag loop is electrically connected to its neighboring zig-zag loop alternately at 90° intervals.

4. The stent according to claim 1, wherein the plurality of electrically conductive elements are disposed in first and second layers.

5. The structure according to claim 4, further including:
   an elastic layer of non-conductive material disposed between the first and second layers.

6. The stent according to claim 5, wherein the conductive elements in the second layer overlay the conductive elements in the first layer and the non-conductive connector nodes connect the conductive elements of the first and second layers such that the currents flowing in the conductive elements of the second layer cancel the currents flowing in the conductive elements of the first layer.

7. The stent according to claim 1, further including:
   a plurality of second electrically conductive struts connected by a plurality of second non-conductive connector nodes to define a diamond-shaped mesh of the second conductive struts, the plurality of second conductive struts and second non-conductive connector nodes being disposed in a second cylinder to define a second generally tubular diamond-shaped conductive mesh, the second conductive struts being electrically connected to define a plurality of second electrically conductive loops of second conductive struts in a zig-zag pattern extending peripherally around the second cylinder, each second loop being electrically connected in such a manner that currents induced in the second loops during a magnetic resonance examination flow in opposite peripheral directions to currents flowing in adjacent loops of the first cylinder and are substantially cancelled by one another.

8. The stent according to claim 7, further including:
   an elastic layer of non-conductive material disposed between the first and second cylinders.

9. The stent according to claim 1, further comprising:
   first and second layers of the diamond shaped mesh with an elastic layer of non-conductive material in between, each conductive mesh layer including a plurality of the electrically conductive struts connected by the non-conductive connector nodes to define a conductive pattern along which the currents induced by the magnetic resonance system flow, the conductive patterns of the first and second conductive mesh layers overlaying each other and being configured such that the current induced in the conductive pattern of the first layer is equal and opposite to the current induced in the conductive pattern of the second layer such that the currents cancel each other.

* * * * *